United States Patent
Webb et al.

(10) Patent No.: US 6,288,060 B1
(45) Date of Patent: Sep. 11, 2001

(54) AMINO SUBSTITUTED PYRIMIDINES AND TRIAZINES

(75) Inventors: Thomas R. Webb, Olivenhain; Terence J. Moran, San Diego; James R. McCarthy, Solana Beach, all of CA (US)

(73) Assignees: Neurocrine Biosciences, Inc., San Diego, CA (US); Janssen Pharmaceutia, N.V., Beerse (BE)

( * ) Notice: Subject to any disclaimer, the term of this patent is extended or adjusted under 35 U.S.C. 154(b) by 0 days.

(21) Appl. No.: 09/051,672

(22) PCT Filed: Oct. 15, 1996

(86) PCT No.: PCT/EP96/04478

§ 371 Date: Apr. 15, 1998

§ 102(e) Date: Apr. 15, 1998

(87) PCT Pub. No.: WO97/14684

PCT Pub. Date: Apr. 24, 1997

Related U.S. Application Data

(60) Provisional application No. 60/005,687, filed on Oct. 17, 1995.

(51) Int. Cl.[7] .................. A61K 31/505; C07D 239/47; C07D 239/45
(52) U.S. Cl. ............ 514/235.8; 514/256; 514/275; 544/122; 544/323; 544/326; 544/329
(58) Field of Search ..................... 544/122, 323, 544/326, 329; 514/235.8, 256, 275

(56) References Cited

U.S. PATENT DOCUMENTS 5,962,479  * 10/1999  Chen ............................. 514/348

FOREIGN PATENT DOCUMENTS

| 0 237 516 A1 | 9/1987 | (EP). |
| 0 576 350 B1 | 12/1993 | (EP). |
| WO 95/10506 | 4/1995 | (WO). |
| WO 95/33750 | 12/1995 | (WO). |

OTHER PUBLICATIONS

De Souza, "Corticotropin–releasing factor receptors: physiology, pharmacology, biochemistry and role in central nervous system and immune disorders," Psychoneuroendocrinology, vol. 20, No. 8, Medline Abstract, 1995.*

Curtis et al., "Corticotropin–releasing factor neurotransmission in *Locus coeruleus*: a possible site of antidepressant action," Brain Res. Bull., vol. 35, No. 5–6, Medline Abstract, 1994.*

Ser. No. 08/255,514, abandoned parent application of Chen, U.S. Patent No. 5962479, Jun. 1994.*

* cited by examiner

Primary Examiner—Richard L. Raymond
(74) Attorney, Agent, or Firm—Scully, Scott, Murphy & Presser

(57) ABSTRACT

Pyrimidines and triazines of formula (I)

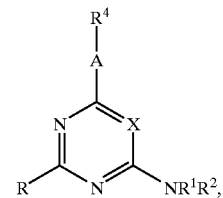

(I)

wherein R is $C_{1-6}$alkyl, amino, mono- or di$C_{1-6}$alkylamino; $R^1$ is hydrogen, $C_{1-6}$alkyl, $C_{3-6}$alkenyl, hydroxy$C_{1-6}$alkyl or $C_{1-6}$alkyloxy-$C_{1-6}$alkyl; $R^2$ is $C_{1-6}$alkyl, mono- or di$C_{3-6}$cycloalkylmethyl, phenylmethyl, substituted phenylmethyl, $C_{1-6}$alkyloxy-$C_{1-6}$alkyl, hydroxy$C_{1-6}$alkyl, $C_{1-6}$alkyloxycarbonyl$C_{1-6}$alkyl, $C_{3-6}$alkenyl; or $R^1$ and $R^2$ taken together with the nitrogen to which they are attached may form a pyrrolidinyl, morpholinyl or piperidinyl group; X is N or $CR^3$; $R^3$ is hydrogen or $C_{1-6}$alkyl; $R^4$ is phenyl or substituted phenyl; A is

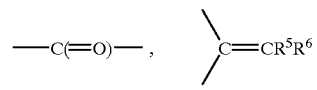

or $—CR^7R^8—$ wherein $R^5$ and $R^6$ each independently are hydrogen or $C_{1-4}$alkyl; $R^7$ is hydrogen or OH, $R^8$ is hydrogen or $C_{1-6}$alkyl; having CRF receptor antagonistic properties; pharmaceutical compositions containing these compounds as active ingredients; methods of treating disorders related to hypersecretion of CRF such as depression, anxiety, substance abuse, by administering an effective amount of a compound of formula (I).

13 Claims, No Drawings

AMINO SUBSTITUTED PYRIMIDINES AND TRIAZINES

CROSS-REFERENCE TO RELATED APPLICATIONS

This application is based upon PCT Application Ser. No. PCT/EP 96/04478, filed Oct. 15, 1996, which claims priority from U.S. Provisional Patent Application Serial No. 60/005,687 filed on Oct. 17, 1995.

BACKGROUND OF THE INVENTION

This invention relates to aminopyrimidines and -triazines which possess CRF receptor antagonistic properties, to pharmaceutical compositions containing these compounds as active ingredient, and the use thereof in the treatment of endocrine, psychiatric and neurologic conditions or illnesses, including stress-related disorders in general.

The first corticotropin-releasing factor (CRF) was isolated from ovine hypothalmi and identified as a 41-amino acid peptide (Vale et al., *Science* 213:1394–1397, 1981). Subsequently, sequences of human and rat CRF were isolated and determined to be identical, but different from ovine CRF in 7 of the 41 amino acid residues (Rivier et al., *Proc. Natl. Acad. Sci. USA* 80:4851, 1983; Shibahara et al., *EMBO J.* 2:775, 1983). CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:13941397, 1981). Briefly, CRF is believed to initiate its biological effects by binding to a plasma membrane receptor which has been found to be distributed throughout the brain (DeSouza et al., *Science* 221:1449–1451, 1984), pituitary (DeSouza et al., *Methods Enzymol.* 124:560, 1986; Wynn et al., *Biochem. Biophys. Res. Comm.* 110:602–608, 1983), adrenals (Udelsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118: 1171–1179, 1986) which mediates CRF-stimulated increase in intracellular production of cAMP (Bilezikjian, L. M., and W. W. Vale, *Endocrinology* 113:657–662, 1983).

In addition to its role in stimulating the production of ACTH and POMC, CRF is also believed to coordinate many of the endocrine autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 2/8332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J. Physiol.* 255:R744, 1988). Furthermore, clinical data suggest that CRF may be hypersecreted in the brain in depression, anxiety-related disorders, and anorexia nervosa. (DeSouza, *Ann. Reports in Med. Chem.* 25:215–223, 1990).

Accordingly, clinical data suggest that CRF receptor antagonists may represent novel antidepressant and/or anxiolytic drugs that may be useful in the treatment of the neuropsychiatric disorders manifesting hypersecretion of CRF. CRF receptor antagonists have been reported in for example, U.S. Pat. No. 5,063,245 disclosing substituted 4-thio-5-oxo-3-pyrazoline derivatives and Australian Patent No. AU-A-41399/93, disclosing substituted 2-aminothiazole derivatives. WO-95/10506 discloses N-alkyl-N-arylpyrimidinamines and derivatives.

Due to the physiological significance of CRF, the development of further biologically active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

DESCRIPTION OF THE INVENTION

This invention is directed to aminopyrimidines and -triazines having the following general structure (I):

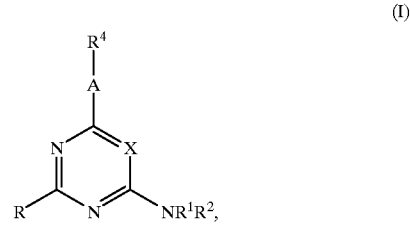

including the stereoisomers and the pharmaceutically acceptable acid addition salt forms thereof, wherein R is $C_{1-6}$alkyl, amino, mono- or di$C_{1-6}$alkylamino;

$R^1$ is hydrogen, $C_{1-6}$alkyl, $C_{3-6}$alkenyl, hydroxy$C_{1-6}$alkyl or $C_{1-6}$alkyloxy$C_{1-6}$alkyl;

$R^2$ is $C_{1-6}$alkyl, mono- or di$C_{3-6}$cycloalkylmethyl, phenylmethyl, substituted phenylmethyl, $C_{1-6}$alkyloxy$C_{1-6}$alkyl, hydroxy$C_{1-6}$alkyl, $C_{1-6}$alkyloxycarbonyl$C_{1-6}$akyl, $C_{3-6}$alkenyl;

or $R^1$ and $R^2$ taken together with the nitrogen atom to which they are attached may form a pyrrolidinyl, morpholinyl or piperidinyl group;

X is N or $CR^3$;

$R^3$ is hydrogen or $C_{1-6}$alkyl;

$R^4$ is phenyl or substituted phenyl;

A is

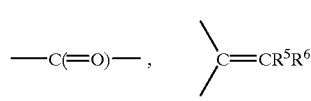

or —$CR^7R^8$— wherein $R^5$ and $R^6$ each independently are hydrogen or $C_{1-4}$alkyl;

$R^7$ is hydrogen or OH;

$R^8$ is hydrogen or $C_{1-6}$alkyl; and substituted phenyl is phenyl substituted with 1, 2 or 3 substituents independently selected from halo, hydroxy, $C_{1-6}$alkyloxy, benzyloxy, $C_{1-6}$alkylthio, trifluoromethyl, $C_{1-6}$alkyl and cyano.

As used in the foregoing definitions halo defines fluoro, chloro, bromo and iodo; $C_{1-2}$alkyl defines straight saturated hydrocarbon radicals having from 1 to 2 carbon atoms such as methyl and ethyl; $C_{2-4}$alkyl defines straight and branched chain saturated hydrocarbon radicals having from 2 to 4 carbon atoms such as ethyl, propyl, butyl, 1-methylethyl and the like; $C_{1-4}$alkyl defines straight and branched chain saturated hydrocarbon radicals having from 1 to 4 carbon atoms such as, methyl, ethyl, propyl, 1-methylethyl, butyl, 1-methylpropyl, 2-methylpropyl and 1,1-dimethylethyl; $C_{1-6}$alkyl defines $C_{1-4}$alkyl radicals as defined hereinbefore and the higher homologs thereof having from 5 to 6 carbon atoms such as, pentyl, the pentyl isomers, hexyl and the hexyl isomers; $C_{3-6}$alkenyl defines straight and branched chain hydrocarbon radicals containing one double bond and having from 3 to 6 carbon atoms such as, for example, 2-propenyl, 2-butenyl, 3-butenyl, 2-methyl-2-propenyl, 2-pentenyl, 3-pentenyl, 3,3-dimethyl-2-propenyl, hexenyl and the like. The carbon atom in the $C_{3-6}$alkenyl moiety being substituted on the $NR^2R^3$-nitrogen preferably is saturated. When $-NR^1R^2$ is a cyclic moiety, it preferably is linked to the pyrimidine or triazine ring through a nitrogen atom.

Depending on the nature of some of the substituents, the compounds of formula (I) may contain one or more asymmetric centers which may be designated with the generally used R and S nomenclature.

The compounds of the present invention are substituted amino compounds and, as such, can be utilized as the free base or in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids.

Particular subgroups of compounds are those wherein one or more of the substituents have the meanings listed herebelow:

R is amino or $C_{1-4}$alkyl; preferably $C_{1-2}$alkyl;

$R^1$ is hydrogen, $C_{1-6}$alkyl or $C_{3-6}$alkenyl; preferably $C_{2-4}$alkyl or $C_{3-4}$alkenyl;

$R^2$ is $C_{1-6}$alkyl, $C_{3-6}$cycloalkylmethyl, hydroxy$C_{1-6}$alkyl, $C_{3-6}$alkenyl, $C_{1-6}$alkyloxycarbonyl$C_{1-6}$alkyl; preferably $R^2$ is $C_{2-4}$alkyl, $C_{3-4}$alkenyl, cyclopropylmethyl, hydroxy$C_{2-4}$alkyl;

or $R^1$ and $R^2$ taken together with the nitrogen atom to which they are attached may form a pyrrolidinyl, morpholinyl or piperidinyl group;

$R^3$ is H or $C_{1-4}$alkyl; preferably $C_{1-2}$alkyl;

A is $-CO-$ or $-CH_2-$;

$R^4$ is phenyl substituted with 2 or 3 substituents selected from halo, $C_{1-4}$alkyloxy and $C_{1-4}$alkyl; preferably phenyl substituted with 2 or 3 substituents selected from methoxy and $C_{1-2}$alkyl.

Other particular subgroups comprises those groups as defined above, wherein X is $CR^3$ or X is N.

Preferred compounds are those wherein X is $CR^3$, wherein $R^3$ is $C_{1-2}$alkyl, R is $C_{1-2}$alkyl, $R^1$ is $C_{2-4}$alkyl, $R^2$ is cyclopropylmethyl, $R^4$ is phenyl di-or trisubstituted in the 2,4,6-position with $C_{1-2}$alkyl or methoxy and A is $-CO-$ or $-CH_2-$. Of these, compounds wherein $R^3$ and R are methyl and $R^1$ is n-propyl are particularly preferred The compounds of the present invention in general can be prepared by reacting a pyrimidine or triazine substituted with a reactive group, e.g. a halopyrimidine or -triazine with a suitable amine:

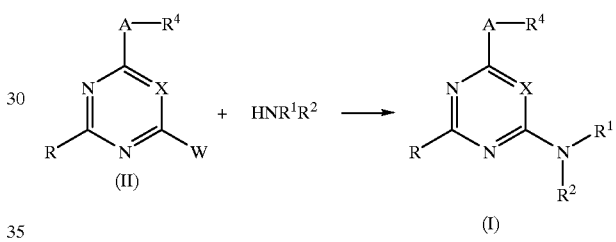

In the above scheme W represents a leaving group, such as halo, e.g. fluoro, chloro, bromo, or a sulfonyloxy group, e.g. a mesyloxy or tosyloxy group. The above reaction typically is done in a suitable solvent, e.g. an aprotic solvent such as DMF or acetonitrile, an ether, e.g. tetrahydrofuran. In case A is a carbonyl group, it may be recommendable to protect it according to art-known procedures.

The compounds of formula (I) may also be prepared by reacting an ester substituted pyrimidine or triazine of formula (III) with a Grignard reagent to yield the corresponding arylketo compound of formula (I-a). The latter may subsequently be derivatized by a subsequent second Grignard reaction to yield the corresponding hydroxyalkyl derivative (I-b), which in turn is dehydrated to the alkenyl derivative of formula (I-c). Or (I-a) may be reduced to the corresponding arylmethyl compound (I-d).

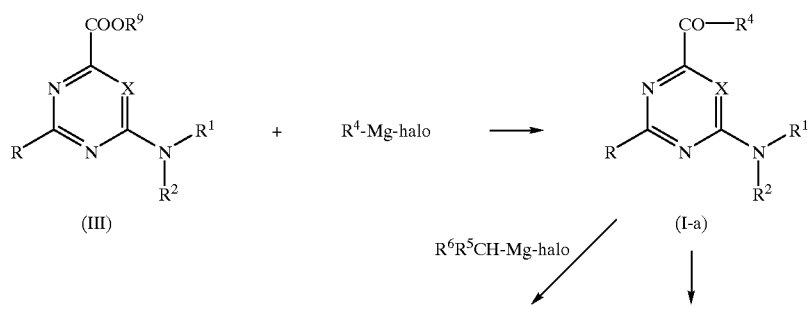

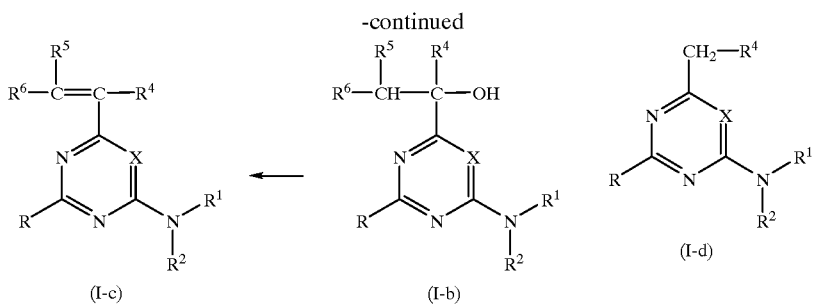

In the above scheme, the group COOR⁹ is an ester group in which $R^9$ in particular is a lower alkyl group, e.g. methyl or ethyl.

The dehydratation reaction to (I-c) can be done by treating (I-b) with methanesulfonyl chloride in the presence of a base.

The reduction to (I-d) e.g. is a hydrogenation procedure, for example by using hydrogen on Pd.

The compounds of formula (I) wherein the central ring is a triazine moiety, being compounds of formula (I-e), can also be prepared by condensing a thiourea (IV) with an imidamide (V).

circumstances, it may be preferable to protect this group. Compounds of formula (I) wherein R is mono- or dialkylamino can be prepared by an alkylation reaction.

The compounds of formula (I) wherein A is a —CR⁸OH—R⁴ group, said compounds being represented by formula (I-f), are prepared via a Grignard procedure, either starting from intermediates (VI) or compounds (I-a). The reduction of (I-f) to (I-g), being compounds of formula (I) wherein A is —CR⁸H—R⁴, typically is conducted with hydrogen on Pd.

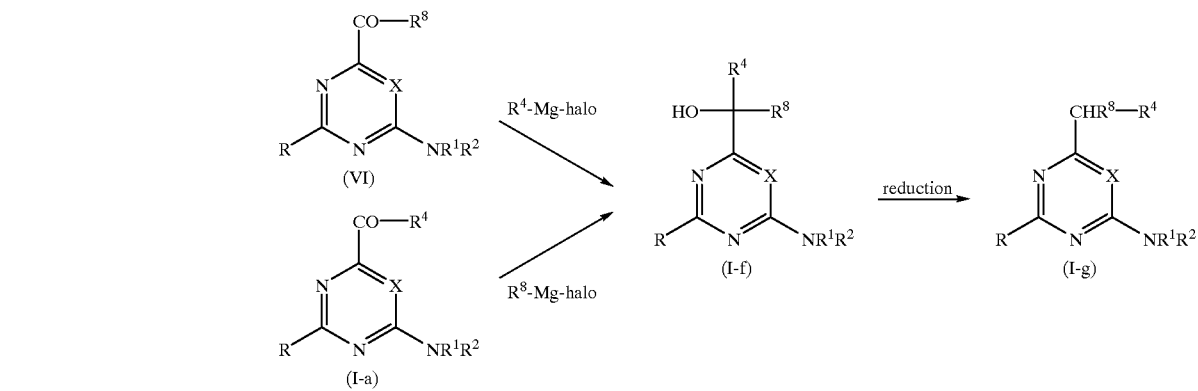

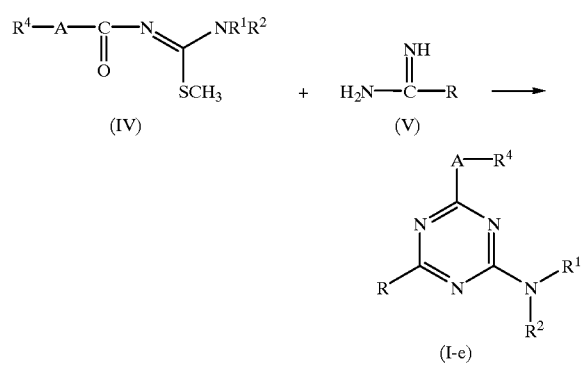

The radical R in the above reaction scheme preferably is amino and A preferably is a ketogroup. This reaction typically is conducted in a suitable solvent e.g. dioxane in the presence of a base such as an alkali metal alkoxide, e.g. potassium tert-butoxide.

Where in any of the aforegoing and following reaction schemes R is an amino group, depending on the reaction The compounds of formula (I) can be converted into each other by art-known functional group transformation reactions. For example, an amino or hydroxy group may be alkylated or in case of an amino group di-alkylated; phenyl groups may be halogenated and halogenated phenyl groups may be converted to the corresponding alkyloxy- or cyanophenyl groups.

Stereoisomers may be prepared by separation of the end products of formula (I) following art-known procedures, e.g. by treatment with an optically active acid and separating the thus-formed diastereoisomeric salts by selective crystallization or column chromatography. Or, stereoisomers may be prepared by using stereoisomeric starting materials in any of the above reaction schemes or in the preparation of intermediates described hereinafter.

The intermediates of formula (II-a), being intermediates of formula (II) wherein W is halo, can be prepared from the corresponding hydroxycarboxyl esters of formula (II-b) analogs by a suitable halogenation reaction, e.g. with POCl₃ or PoBr₃, followed by a Grignard reaction. The hydroxy analogs in turn can be prepared as follows:

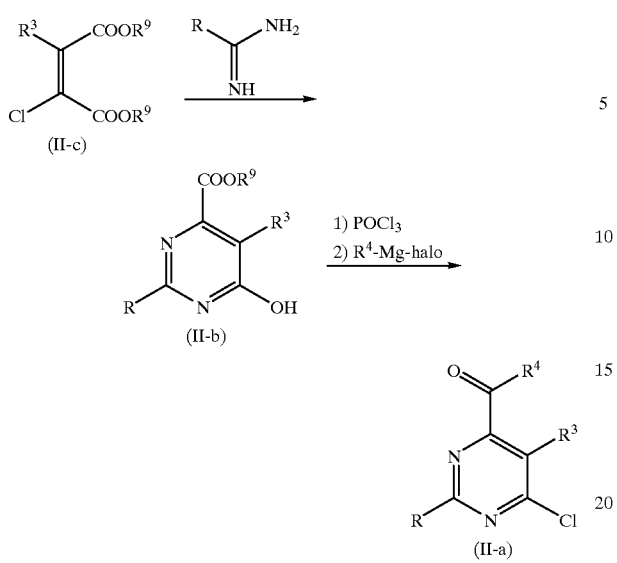

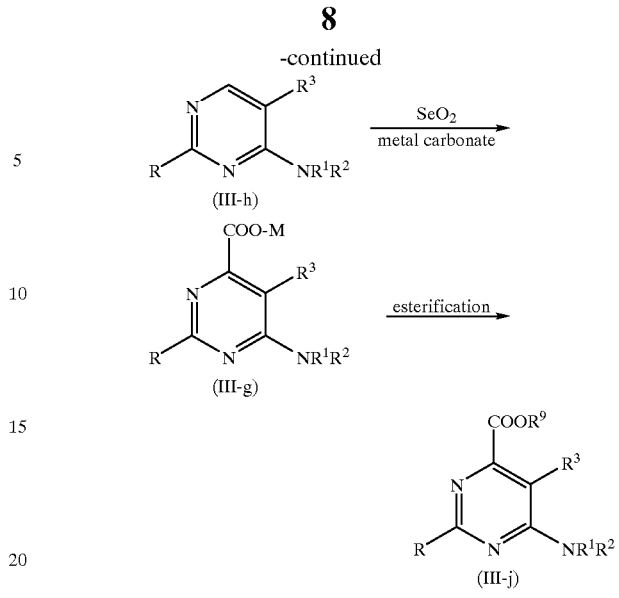

The intermediates (VI) are prepared in an analogous fashion.

The carbonyl group in formula (II-a) may further be converted to the corresponding $CH_2$ group by a reduction procedure similar to the above-mentioned reduction of (I-a) to (I-d) or to an alkenyl group similar as the reaction of (I-a) to (I-c).

The intermediates of formula (II-c) can be prepared as described hereinbelow for the preparation of the intermediates (III-c) which have the same structure.

The intermediates of formula (III) wherein X is $CR^3$ can be prepared according to the following reaction scheme:

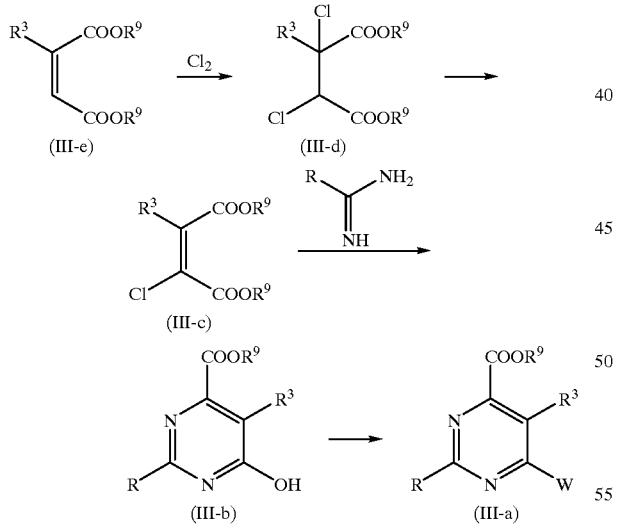

The same intermediates of formula (II) can also be prepared as follows:

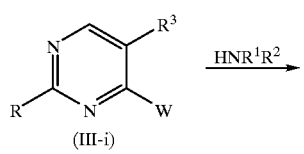

In the above scheme, W and $R^9$ have the previously mentioned meaning and M is a metal kation. Intermediate (III-i) is treated with an amine to yield (III-h) which subsequently is treated with $SeO_2$ and a metal carbonate or hydrogen carbonate, wherein the metal preferably is an alkalimetal, e.g. $NaHCO_3$, $CS_2CO_3$, in order to introduce a carboxyl group. The intermediate (III-g) is esterified, e.g. with $SOCl_2$ in an alcohol to obtain intermediates of formula (III-j).

The intermediates of formula (IV) are prepared from the corresponding keto-esters of formula (IV-a) as follows:

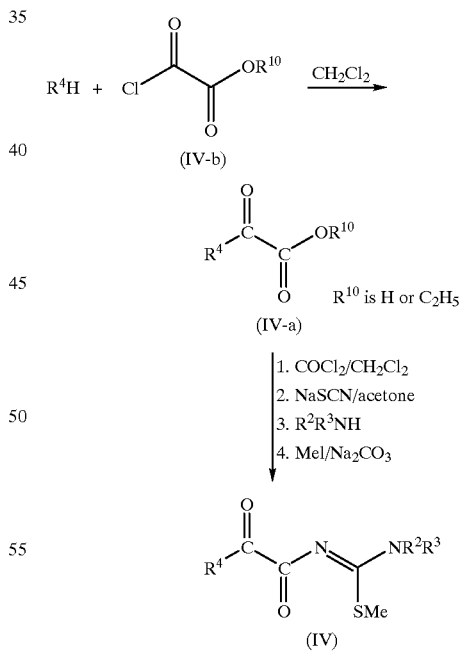

In the above scheme $R^{10}$ is hydrogen or lower alkyl, e.g. ethyl.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g. [$^{125}$I]tyrosine CFR) to receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)). With reference to CRF receptor binding affinities, CRF receptor antagonists of this invention have a $K_i$ of less than 10 mM. In a preferred embodiment of this invention, a CRF receptor antagonist has a $K_i$ of less than 1 mM, and more preferably less than 0.25 mM (i.e., 250 nM).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder, that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, USA, 1990.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

The following examples are provided for purposes of illustration, not limitation.

EXPERIMENTAL PART

EXAMPLE 1

Preparation of 4-amino-pyrimidine-6-carboxylic Acid, Esters

1a) A solution of 4-chloro-2,5-dimethylpyrimidine-6-carboxylic acid, ethyl ester (10 mmol) (described as compound 11 in *J. Org. Chem.*, 46, p 1413–1412 (1981)) and substituted amine (5 ml), was refluxed for 4 hours in acetonitrile, or the mixture was heated for 3 hours at 120° C., neat. This was allowed to cool to room temperature. Subsequently, the reaction mixture was worked up by one of the following procedures. (1) It was diluted with hexane and filtered, the filtrate was concentrated and the residue was purified by $SiO_2$ chromatography (EtOAc/hexane). Or (2) by concentrating the mixture and purification by $SiO_2$ chromatography (EtOAc/hexane). This yielded the desired 4-alkylamino-2,5-dimethylpyrimidine-6-carboxylic acid, esters. So, using this procedure starting from 2.8g (13 mmol) of the said pyrimidine ethyl ester and an excess of N-propyl-N-cyclopropylmethylamine, there was obtained 2,5-dimethyl-4-(N-propyl-N-cyclopropylmethyl-amino)-pyrimidine-6-carboxylic acid, ethyl ester.

1b) A solution of 2,6dimethyl-4-chloropyrimidine (1.7 g, 11 mmol) in 15 ml of dipropylamine was allowed to reflux for 18 hours. The solution was allowed to cool to room temperature and then poured into ethyl acetate/water. The organic phase was washed with water, followed by brine, dried ($MgSO_4$) and concentrated. This gave 2.3g of a yellow oil. Proton NMR indicated that this was pure 2,6-dimethyl-4-(N,N-dipropyl)pyrimidine. This material was used directly for subsequent steps.

1c) A solution of 2,4-dimethyl-6-(N,N-dipropyl)-pyrimidine (1.73 g, 8.4 mmol) in 13 ml dry pyridine, was treated with $SeO_2$ (1.18 g, 10 mmol). This suspension was refluxed for 5 hours, allowed to cool then diluted with 100 ml of water, and filterd The filtrate is concentrated under vacuum, diluted with water and concentrated again. This residue was dissolved in sufficient saturated $NaHCO_3$ to give a mixture at pH 8 and washed twice with ethyl acetate. The aqueous phase was concentrated to dryness. This solid residue was suspended in 20 ml dry methanol and 2 ml of $SOCl_2$. This suspension was stirred for 20 hours at 22° C. This mixture was diluted with water and neutralized with $NaHCO_3$, then extracted with EtOAc. The organic phase was washed with brine, dried ($MgSO_4$) and concentrated. The residue was purified by flash chromatography (0–40% EtOAc/hexane) to give 2-methyl-4-(N,N-dipropyl)-pyrimidine-6-carboxylic acid, methyl ester. On standing, this material crystallized, m.p.=45–46° C.

1d) A solution of 2,6-dimethyl-4-chloropyrimidine (4.4 g, 30.9 mmol) and N-propyl-N-cyclopropylmethylamine (7.2 g, 64 mmol) was allowed to reflux for 10 hours. The solution was allowed to cool to room temperature and then poured into ethyl acetate/water. The organic phase was washed with water, then brine, dried ($MgSO_4$) and concentrated. This gave 6.4 g of the yellow oil. Proton NMR indicated that this was 2,6-dimethyl-4-(N-propyl-N-cyclopropylmethylamino) pyrimidine. This material was used directly for subsequent steps.

1e) A solution of 2,6-dimethyl-4-(N-propyl-N-cyclopropylmethylamino)pyrimidine (2.2 g, 10 mmol) in 15 ml dry pyridine, was treated with $SeO_2$ (1.4 g, 12.5 mmol). This suspension was refluxed for 5 hours, allowed to cool then diluted with 100 ml of water, and filterer The filtrate is concentrated under vacuum, diluted with water and concentrated again. The residue was partitioned between a solution of 1.65 g of $Cs_2CO_3$ in 100 ml water and ethyl acetate. The aqueous phase was washed with ether and concentrated to dryness. After drying under high vacuum overnight the residue was suspended in 60 ml of DMF and concentrated, this residue was suspended again and reconcentrated. This residue was then suspended in 60 ml DMF and 2 ml of iodo-methane was added. This suspension was stirred for 5 hours at 22° C. This mixture was diluted with water and extracted with EtOAc. The organic phase was washed with brine, dried($MgSO_4$) and concentrated. The residue was purified by flash chromatography (10–40% EtOAc/hexane) to give 2-methyl-4-(N-propyl-N-cyclopropylmethylamino)-pyrimidine-6-carboxylic acid, methyl ester (350 mg). TLC (50% EtOAxc/hexane, $R_f$=0.4).

1f) Ethyl ethoxalyl butyrate was prepared by analogous procedure to methyl ethoxalyl butyrate (*Org. Syn. Coll. Vol.* 2, 272–273). This compound was converted to 4-hydroxy-2-methyl-5-ethyl-pyrimidine-6-carboxylic acid, ethyl ester which was subsequently converted to 4-chloro-2-methyl-5-ethyl-pyrimidine-6-carboxylic acid, ethyl ester using the method of S. Hecht, et al. (*J. Org. Chem.*, 46, 1413–1423 (1981)).

EXAMPLE 2

Preparation A of 6-phenylketopyrimidines

A solution of the appropriate 4-(N-alkylamino) pyrimidine-6-carboxylic acid ester derivative (0.4 mmol) in 5 ml of THF (under an atmosphere of nitrogen) was cooled to −78° C. and treated with a 1M solution of the substituted Grignard reagent in THF (0.8 ml), with good stirring. After 1 hour this solution was allowed to slowly warm to room temperature. The reaction mixture was poured into water and extracted with EtOAc. The organic extracts were washed with brine, dried ($MgSO_4$) and concentrated. The residue was purified by $SiO_2$ chromatography (EtOAc/hexane) to give 4-(N-alkylamino)-6-(substituted phenylketo)-pyrimidine derivatives.

EXAMPLE 3
Preparation B of 6-phenylketopyrimidines

3a) A solution of 2,5-dimethyl4-chloro-pyrimidine-6-carboxylic acid, ethyl ester (3.2 g, 30 mmol) in 70 ml of THF was cooled to −78° C. and 50 ml of a 1M solution of mesitylene magnesium bromide was added dropwise. This solution was allowed to slowly warm to room temperature. The reaction mixture was poured into a solution of 6 g of $NH_4Cl$ in 300 ml of water, and extracted with $CHCl_3$. The organic phase was washed with brine, dried and concentrated. The residue was purified by $SiO_2$ chromatography (20% EtOAc/hexane) to give 3.2 g of 2,5-dimethyl-4-chloro-6-(2',4',6'-trimethylphenylketo)pyrimidine.

3b) A solution of the appropriate 2,5-dimethyl-4-chloro-6-(2',4',6'-trimethylphenylketo)pyrimidine (100 mg, 0.3 mmol) in 1 ml of acetonitrile was refluxed with 1.5 mmol of substituted amine with good stirring. After 4 hours this solution was allowed to cool to room temperature. The reaction mixture was poured into water and extracted with EtOAc. The organic extracts were washed with brine, dried ($MgSO_4$) and concentrated. The residue was purified by $SiO_2$ chromatography (EtOAc/hexane) to give 4-(N-alkylamino)-6-(substituted phenylketo)-pyrimidine derivatives.

EXAMPLE 4
Preparation C of 6-phenylketopyrimidines

4a) To a solution of mesitylene (35 ml, 0.251 mol) and ethyl oxalyl chloride (36.4 g, 0.266 mol) in dichloromethane (150 ml) was added portionwise aluminum chloride (35.2 g, 0.265 mol) at 0° C. The resulting red solution was stirred at 0° C. for 1 hour, then at r.t. overnight. The reaction was carefully quenched with ice when the flask cooled with ice-water bath. The mixture was extracted with ethyl acetate (500+200 ml). The extract was washed with brine, saturated $NaHCO_3$ and brine, dried over $MgSO_4$, filtrated and concentrated in vacuo to give ethyl mesitylglyoxylate as a yellowish oil (34 g, 60%). $^1H$ NMR δ 1.40 (t, 3H), 2.28 (s, 6H), 2.33 (s, 3H), 4.40 (q, 2H), 6.90 (s,2H).

The aqueous $NaHCO_3$ phase was acidified with concentrated HCl to pH 3, and extracted with ethyl acetate (2×200 ml). The extract was washed with brine, dried over $MgSO_4$, filtered and concentrated in vacuo to give mesitylglyoxylic acid as a yellowish solid (19.5 g, 40%) $^1H$ NMR δ 2.21(s, 6H 2.34(s; 3H), 6.65 (brs, 1H), 6.93 (s, 2H)

4b) Mesitylglyoxylic acid (1.92 g, 10 mmol) was dissolved in dichloromethane (30 ml). Oxalyl chloride (2 ml, 23 mmol) was added followed by 1 drop of DMF. The mixture was stirred at room temperature for 1 hour. The excess oxalyl chloride and solvent were removed in vacuo. The acid chloride was dissolved in acetone (5 ml) and added into a solution of sodium thiocyanate (1.0 g, 12 mmol) in acetone (30 ml) at 0° C. with vigorous stirring. After ten minutes n-propylcyclopropanemethylamine (1.13 g, 10 mmol) was added and the yellow suspension was stirred at 0° C. for 30 minutes. Sodium carbonate (1.3 g, 12.5 mmol) and methyl iodide (2.84 g, 20 mmol) were added and the mixture was stirred at room temperature overnight. The suspension then was partitioned in ethyl acetate-water (200–50 ml), and the organic layer was washed with brine, dried over $MgSO_4$, filtered and evaporated in vacuo to give a yellow oil which was purified by chromatography (1:3 to 1:1 ethyl acetate-hexanes). The S-methyl-N-acylthiourea was obtained as a yellowish oil (1.5 g, 42%). $^1H$ NMR δ 0.15–1.75 (m, 10H), 2.27 (s, 6H), 2.43 (s, 3H), 3.39 (d, 2H), 3.51 (m, 2H), 6.82 (s, 2H).

4c) The thiourea, obtained above (20 mg, 0.056 mmol) was mixed with guanidine hydrochloride (50 mg, 0.53 mmol) and potassium t-butoxide (55 mg, 0.49 mmol) in dioxane (2 ml). The suspension was heated to reflux for 3 hours. The product was purified by preparative TLC with 1:3 Ethyl acetate-Hexanes, colorless oil, 7 mg. $^1H$ NMR δ 0.30 (m,2H), 0.62 (m, 2H), 0.96 (t, 3H), 1.05 (m,1H), 1.65 (m, 2H), 2.24 (s,6H), 2.30 (s, 3H), 3.25 (d, 2H), 3.40 (t, 3H), 6.87 (s,2H), 8.75 (br s, 2H).

EXAMPLE 5

[6-[(cyclopropylmethyl)[propylamino](2,5-dimethyl-4-pyrimidinyl)(2,4,6-trimethoxy-phenyl)methanone (100 mg, 0.24 mmol) in 1 ml $CH_2Cl_2$ was cooled in an ice-bath and 1.2 ml of 2M trimethylaluminum was added dropwise followed by trimethylsilyltriflate (0.48 ml, 2.4 mmol). This solution was allowed to stir at 5° C. for 1 hour at room temperature for 3 hours. The reaction mixture was poured into 5% $NaHCO_3$ and extracted with ethyl acetate, the organic phase was dried ($MgSO_4$) and concentrated. Preparative TLC (50% EtOAc/hexane) gave the gem-dimethyl derivative and [6-[(2,4,6-trimethoxyphenyl)2-2ethenyl]-2,5-dimethyl-N-propyl-N-cyclopropylmethyl-4-pyrimidinamine (30 mg) (compund 9).

EXAMPLE 6

6a) To a solution of 413 mg (1.00 mmol) of 2,5-dimethyl-4-(N-propyl-N-cyclopropylmethylamino)-6-(2',4',6'-trimethyloxyphenylketo)pyrimidine in 50 ml THF at −78° C. was added 1.5 ml of 2.0 M isopropyl magnesium chloride (3.0 mmol) in THF. After TLC (EtOAc) indicated starting material was consumed, the solution was quenched with aqueous sodium bicarbonate, warmed to room temperature, extracted with chloroform and evaporated under reduced pressure. After NMR analyis, the alcohol (6-[(cyclopylmethyl)propylamino]-2,5-dimethyl-α-(1methylethyl)-α-(2,4,6-trimethoxyphenyl)-4-pyrimidinemethanol was used in the next step without purification.

The alcohol (from above) was dissolved in 50 ml of chloroform. 1 ml of $Et_3N$ and ml of methanesulfonyl chloride were added. After 30 minutes at room temperature, eous sodium bicarbonate was added. The mixture was extracted with 200 ml itional chloroformn and concentrated. The olefin (6-[2'-(2",4",6"-trimethoxyphenyl)-propenyl]-2,5-dimethyl-4-(N-propylcyclopropylmethylamino)-pyrimidine) was ained after 2 chromatography separations.

EXAMPLE 7

2,5Dimethyl-4-(N-propyl-N-cyclopropylmethylamino)-6-(2',4',6'-trimethyloxyphenylketo)pyrimidine (50 mg, 0.12 mmol) in 5 ml of glacial acetic acid was treated with 50 mg of 10% Pd on active carbon and shaken under 3.45 $10^5$ Pa hydrogen for 4 hours. The mixture was filtered, concentrated, and purified by prep. TLC (60% EtOAc/hexane) to give 20 mg of 2,6-dimethyl-4-(N-propyl-N-cyclopropylmethylamino)-6-(2',4',6'-trimethyloxyphenylmeth-1'-yl)-pyrimidine (compound 20).

The following tables list a number of compounds which can be made according to any of the above described procedures.

TABLE 1

[Structure: 2,4,6-trisubstituted phenyl (Rᵃ, Rᵇ, Rᶜ) connected via A to a pyrimidine with R at 2-position, R³ at 5-position, and N(R¹)(R²) at 4-position]

| Co No. | R³ | R | R¹ | R² | A | Rᵃ | Rᵇ | Rᶜ | Proc |
|---|---|---|---|---|---|---|---|---|---|
| 1 | H | CH$_3$ | (CH$_2$)$_2$CH$_3$ | (CH$_2$)$_2$CH$_3$ | >C=O | CH$_3$ | CH$_3$ | CH$_3$ | A |
| 2 | CH$_3$ | CH$_3$ | (CH$_2$)$_2$CH$_3$ | CH$_2$-cyclopropyl | >C=O | CH$_3$O | CH$_3$O | CH$_3$O | A |
| 3 | H | CH$_3$ | (CH$_2$)$_2$CH$_3$ | CH$_2$-cyclopropyl | >C=O | CH$_3$O | CH$_3$O | CH$_3$O | A |
| 4 | H | CH$_3$ | (CH$_2$)$_2$CH$_3$ | CH$_2$-cyclopropyl | >C=O | CH$_3$ | CH$_3$ | CH$_3$ | A |
| 5 | CH$_3$ | CH$_3$ | (CH$_2$)$_2$CH$_3$ | CH$_2$-cyclopropyl | >C=O | CH$_3$ | CH$_3$ | CH$_3$ | A |
| 6 | CH$_3$ | CH$_3$ | (CH$_2$)$_2$CH$_3$ | CH$_2$-cyclopropyl | >C=O | CH$_3$O | CH$_3$O | H | A |
| 7 | CH$_3$ | CH$_3$ | CH$_2$CH$_3$ | —(CH$_2$)$_3$—CH$_3$ | >C=O | CH$_3$O | CH$_3$O | CH$_3$O | A |
| 8 | CH$_3$ | CH$_3$ | (CH$_2$)$_2$CH$_3$ | CH$_2$-cyclopropyl | >C=O | C$_2$H$_5$ | C$_2$H$_5$ | C$_2$H$_5$ | A |
| 9 | CH$_3$ | CH$_3$ | (CH$_2$)$_2$CH$_3$ | CH$_2$-cyclopropyl | >C=CH$_2$ | CH$_3$O | CH$_3$O | CH$_3$O | Ex. 5 |
| 10 | CH$_3$ | CH$_3$ | (CH$_2$)$_2$OCH$_3$ | (CH$_2$)$_2$OCH$_3$ | >C=O | CH$_3$ | CH$_3$ | CH$_3$ | B |
| 11 | CH$_3$ | CH$_3$ | (CH$_2$)$_2$CH$_3$ | (CH$_2$)$_2$OH | >C=O | CH$_3$ | CH$_3$ | CH$_3$ | B |

TABLE 1-continued

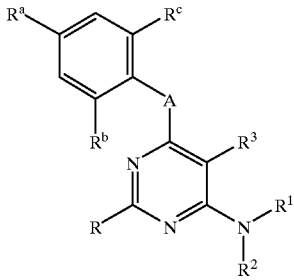

| Co No. | R³ | R | R¹ | R² | A | Rᵃ | Rᵇ | Rᶜ | Proc |
|---|---|---|---|---|---|---|---|---|---|
| 12 | CH₃ | CH₃ | CH₂CH₃ | CH₂-phenyl | \C=O | CH₃ | CH₃ | CH₃ | B |
| 13 | CH₃ | CH₃ | (CH₂)₂CH₃ | (CH₂)₂CH₃ | \C=O | CH₃ | CH₃ | CH₃ | B |
| 14 | CH₃ | CH₃ | CH₂CH=CH₂ | CH₂—CH=CH₂ | \C=O | CH₃ | CH₃ | CH₃ | B |
| 15 | CH₃ | CH₃ | H | (CH₂)₂OCH₃ | \C=O | CH₃ | CH₃ | CH₃ | B |
| 16 | CH₃ | CH₃ | (CH₂)₂CH₃ | CH₂-cyclopropyl | \C=CH(C₂H₅) | CH₃O | CH₃O | CH₃O | Ex. 6 |
| 17 | CH₃ | CH₃ | H | CH₂—COOC₂H₅ | \C=O | CH₃ | CH₃ | CH₃ | B |
| 18 | CH₃ | CH₃ | H | (CH₂)₂phenyl | \C=O | CH₃ | CH₃ | CH₃ | B |
| 19 | CH₃ | CH₃ | (CH₂)₂CH₃ | CH₂-cyclopropyl | \C=C(CH₃)(CH₃) | CH₃O | CH₃O | CH₃O | Ex. 6 |
| 20 | CH₃ | CH₃ | (CH₂)₂CH₃ | CH₂-cyclopropyl | \C=CH₂ | CH₃O | CH₃O | CH₃O | Ex. 5 |
| 21 | CH₃ | CH₃ | (CH₂)₂CH₃ | CH₂-phenyl | \C=O | CH₃ | CH₃ | CH₃ | B |
| 22 | CH₃ | C₂H₅ | (CH₂)₂CH₃ | CH₂-cyclopropyl | \C=O | CH₃ | CH₃ | CH₃ | A |

TABLE 2

| Co No | R³ | R | Z | A | Rᵃ | Rᵇ | Rᶜ | Proc. |
|---|---|---|---|---|---|---|---|---|
| 23 | CH₃ | CH₃ | morpholinyl | C=O | CH₃ | CH₃ | CH₃ | B |
| 24 | CH₃ | CH₃ | pyrrolidinyl | C=O | CH₃ | CH₃ | CH₃ | B |

TABLE 3

| Co No | R | R¹ | R² | Rᵃ | Rᵇ | Rᶜ | Proc. |
|---|---|---|---|---|---|---|---|
| 25 | NH₂ | n-propyl | CH₂-cyclopropyl | CH₃ | CH₃ | CH₃ | C |

The analytical data for compounds in tables 1 to 3 are summarized in table 6.

TABLE 4

| Co. No. | R¹ | R² | Proc | Mass spectral data [M + 1⁺] |
|---|---|---|---|---|
| 26 | (CH₂)₂—CH₃ | c. propyl-methyl | A | 338 |

TABLE 5

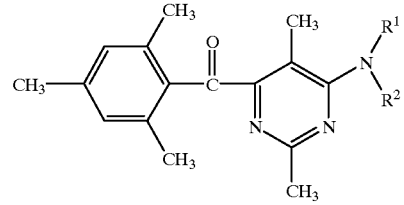

| Co. No. | R¹ | R² | Proc | Mass spectral data [M⁺] |
|---|---|---|---|---|
| 27 | CH₃ | CH₃ | B | 297 |
| 28 | H | (CH₂)₅—CH₃ | B | 353 |
| 29 | (CH₂)₃—CH₃ | (CH₂)₃—CH₃ | B | 381 |
| 30 | CH₃ | phenylmethyl | B | 373 |
| 31 | H | CH₃ | B | 283 |
| 32 | (CH₂)₃—CH₃ | phenylmethyl | B | 415 |
| 33 | H | 4-chlorophenylmethyl | B | 393 |
| 34 | H | 4-(trifluoromethyl)-phenylmethyl | B | 427 |
| 35 | H | c.hexylmethyl | B | 365 |
| 36 | H | 2-methylphenylmethyl | B | 373 |
| 37 | 1-methylethyl | 1-methylethyl | B | 353 |
| 38 | H | 3,4-dimethoxyphenylmethyl | B | 415 |
| 39 | CH₂—CH₃ | CH₂—CH₃ | B | 325 |
| 40 | H | 2-chlorophenylmethyl | B | 394 |
| 41 | H | 3,4-dichlorophenylmethyl | B | 429 |
| 42 | H | 3,4,5-trimethoxyphenylmethyl | B | 449 |
| 43 | CH₂—CH₂OH | phenylmethyl | B | 403 |
| 44 | H | 2,3-dimethoxyphenylmethyl | B | — |
| 45 | H | 2-propenyl | B | 309 |
| 46 | H | phenylmethyl | B | 359 |
| 47 | CH₂—CH₂OH | CH₂—CH₂OH | B | 357 |
| 48 | H | c.propylmethyl | B | 324 |
| 49 | CH₂—CH₃ | 2-methyl-2-propenyl | B | 351 |
| 50 | H | (CH₂)₃—CH₃ | B | 325 |
| 51 | H | 1,1-dimethylethyl | B | 325 |
| 52 | CH₂—CH₃ | (CH₂)₃—CH₃ | B | 353 |
| 53 | H | 3,5-dimethoxyphenylmethyl | B | 419 |
| 54 | H | 1-methylbutyl | B | 339 |
| 55 | H | 2-(trifluoromethyl)-phenylmethyl | B | 427 |
| 56 | H | (CH₂)₂—CH₃ | B | 311 |
| 57 | H | 2-fluorophenylmethyl | B | 377 |
| 58 | H | 2-methoxyphenylmethyl | B | 389 |
| 59 | H | 2-ethoxyphenylmethyl | B | 403 |
| 60 | H | 3-methylphenylmethyl | B | 373 |
| 61 | H | 3-fluorophenylmethyl | B | 377 |
| 62 | H | 4-methylphenylmethyl | B | 373 |
| 63 | H | 4-fluorophenylmethyl | B | 377 |
| 64 | H | 4-methoxyphenylmethyl | B | 389 |
| 65 | H | 2,6-difluorophenylmethyl | B | 395 |
| 66 | (CH₂)₃—O—CH₃ | 3,4,5-trimethoxyphenylmethyl | B | 521 |
| 67 | H | CH₂—CH₃ | B | 297 |
| 68 | H | 1-methylethyl | B | 311 |
| 69 | H | 1-methylpropyl | B | 325 |
| 70 | H | 2-methoxypropyl | B | 325 |
| 71 | H | 3-methylbutyl | B | 339 |
| 72 | H | 1,2-dimethylpropyl | B | 339 |
| 73 | H | 1,3-dimethylbutyl | B | 353 |
| 74 | H | 3,3-dimethylbutyl | B | 353 |
| 75 | CH₃ | (CH₂)₂—CH₃ | B | 325 |
| 76 | H | (CH₂)₃—O—CH₂—CH₃ | B | 355 |
| 77 | CH₃ | 2-propenyl | B | 323 |
| 78 | H | 3-trifluorophenylmethyl | B | — |
| 79 | H | (CH₂)₄—CH₃ | B | — |
| 80 | H | (CH₂)₃—OCH₃ | B | — |
| 81 | H | CH(CH₃)(CH₂OCH₃) | B | — |
| 82 | H | (CH₂)₃OCH(CH₃)₂ | B | 369 |
| 83 | H | (CH₂)₂OH | B | — |
| 84 | H | (CH₂)₃OH | B | — |
| 85 | H | CH(CH₂CH₃)₂ | B | 339 |
| 86 | H | CH(CH₂OH)(CH₂)₃CH₃ | B | 369 |
| 87 | H | CH(CH₂OH)(CH₂)₂CH₃ | B | 355 |
| 88 | —(CH₂)₅— (*) | | B | 337 |

(*): R¹ and R² taken together

TABLE 6

Analytical data

| Co. No. | $^1$H NMR data (CDCl$_3$) | MS |
|---|---|---|
| 1 | δ 0.89(t, J=7.5Hz, 6H), 1.59(m, 4H), 2.12(s, 6H), 2.32(s, 3H), 2.51(s, 3H), 3.38(bs, 4H), 6.65(s, 1H), 6.87(s, 2H). | 339 |
| 2 | δ 0.15(m, 2H), 0.47(m, 2H), 0.85(t, J=7.5Hz, 3H), 1.05 (m, 1H), 3.37(t, 2H), 1.57(m, 2H), 2.17(s, 3H), 2.43(s, 3H), 3.23(d, 2H), 3.63(s, 6H), 3.83(s, 3H), 6.07(s, 2H). | 413 |
| 3 | | 398 |
| 4 | δ 0.22(m, 2H), 0.49(m, 2H), 0.85(t, J=7.5Hz, 3H), 1.05 (m, 1H), 1.60(m, 2H), 2.10(s, 6H), 2.30(s, 3H), 2.50(s, 3H), 3.43(bs, 4H), 6.70(s, 1H), 6.86(s, 2H). | 351 |
| 5 | δ 0.15(m, 2H), 0.48(m, 2H), 0.87(t, J=7.5Hz, 6H), 1.02 (m, 1H), 1.25(m, 2H), 2.11(s, 6H), 2.17(s, 3H), 2.27(s, 3H), 2,38(s, 3H), 3.23(d, 2H), 3.42(m, 2H), 6.82(s, 2H). | 365 (M$^+$) |
| 6 | | 383 |
| 7 | δ 0.91(t, J=7.5Hz, 3H), 1.16(t, J=7.5Hz, 3H), 1.28(m, 2H), 1.53(m, 2H), 2.16(s, 3H), 2.42(s, 3H), 3.37(m, 4H), 3.63(s, 6H), 3.82(s, 3H), 6.09(s, 2H). | |
| 8 | δ 0.19(m, 2H), 0.50(m, 2H), 0.87(t, J=7.5Hz, 3H), 1.02 (m, 1H), 1.12(t, J=7Hz, 6H), 1.25(t, J=7Hz, 3H), 1.61(m, 2H), 2.36(s, 3H), 2.39(s, 3H), 2.45(q, J=7Hz, 4H), 2.65 (q, J=7Hz, 2H), 3.25(d, 2H), 3.44(m, 2H), 6.93(s, 2H). | 407 |
| 9 | δ 0.15(m, 2H), 0.47(m, 2H), 0.85(t, J =7.5Hz, 3H), 1.05 (m, 1H), 1.37(t, 2H), 1.57(m, 2H), 1.78(s, 3H), 2.53(s, 3H), 3.23(d, 2H), 3.31(t, 2H), 3.63(s, 6H), 3.83(s, 3H), 5.62(s, 1H), 5.94(s, 1H), 6.11(s, 2H) | M-1 = 410 |
| 10 | δ 2.12(s, 6H), 2.27(s, 3H), 2.29(s, 3H), 2.39(s, 3H), 3.31 (s, 6H), 3.55(t, 4H), 3.67(t, 4H), 6.83(s, 2H). | 385 |
| 11 | δ 0.93(t, 3H), 1.66(m, 2H), 2.23(s, 6H), 2.29(s, 3H), 2.32(s, 3H), 2.41(s, 3H), 3.29(m, 2H), 3.68(m, 2H), 3.87(m, 2H), 6.84(s, 2H). | |
| 12 | δ 1.19(t, 3H), 2.23(s, 6H), 2.29(s, 3H), 2.32(s, 3H), 2.41 (s, 3H), 3.42(q, 2H), 4.67(s, 2H), 6.84(s, 2H), 7.25–7.35 (m, 5H). | 387 |
| 13 | δ 0.89(t, 6H), 1.62(m, 4H), 2.12(s, 6H), 2.27(s, 3H), 2.29(s, 3H), 2.39(s, 3H), 3.35(t, 4H), 6.83(s, 2H). | 353 |
| 14 | δ 2.12(s, 6H), 2.27(s, 3H), 2.29(s, 3H), 2.39(s, 3H), 3.99 (d, 2H), 5.22(m, 4H), 5.93(m, 2H), 6.84(s, 2H). | 349 |
| 15 | δ 2.23(s, 6H), 2.29(s, 3H), 2.32(s, 3H), 2.41(s, 3H), 3.41 (s, 3H), 3.58(t, 2H), 3.74(m, 2H), 6.84(s, 2H). | |
| 16 | δ 0.15(m, 2H), 0.47(m, 2H), 0.80(t, J=7.5Hz, 3H), 0.97(t, 3H), 1.90(s, 3H), 2.50(s, 3H), 3.13(d, 2H), 3.31(t, 2H), 3.63(s, 6H), 3.83(s, 3H), 6.07(s, 2H). | 439 |
| 17 | δ 1.32(t, J=7Hz, 3H), 2.23(s, 6H), 2.29(s, 3H), 2.32(s, 3H), 2.41(s, 3H), 4.35(m, 4H), 6.84(s, 2H). | 355 |
| 18 | δ 2.23(s, 6H), 2.29(s, 3H), 2.32(s, 3H), 2.41(s, 3H), 2.98 (t, J=7Hz, 2H), 3.82(t, J=7Hz, 2H), 6.84(s, 2H). | |
| 19 | δ 0.15(m, 2H), 0.47(m, 2H), 0.80(t, J=7.5Hz, 3H), 0.97 (m, 1H), 1.49(m, 2H), 1.63(s, 3H), 1.78(s, 3H), 1.94(s, 3H), 2.43(s, 3H), 3.13(d, 2H), 3.31(t, 2H), 3.63(s, 6H), 3.83(s, 3H), 6.07(s, 2H). | 439 |
| 20 | δ 0.04(m, 2H), 0.47(m, 2H), 0.80(t, J =7.5Hz, 3H), 1.05 (m, 1H), 1.50(m, 2H), 1.94(s, 3H), 2.45(s, 3H), 3.07(d, 2H), 3.27(t, 2H), 3.61(s, 6H), 3.80(s, 3H), 3.92(s, 2H), 6.11(s, 2H) | M-1 = 399 |
| 22 | δ 0.15(m, 2H), 0.48(m, 2H), 2.11(s, 6H), 2.17(s, 3H), 2.38(s, 3H), 2.80(q, 2H), 3.28(d, 2H), 3.42(m, 2H), 6.82(s, 2H) | M$^+$ = 379 |
| 23 | δ 2.12(s, 6H), 2.27(s, 3H), 2.29(s, 3H), 2.39(s, 3H), 3.37 (t, 4H), 3.83(t, 4H), 6.83(s, 2H). | 339 |
| 24 | δ 1.95(t, 4H), 2.12(s, 6H), 2.27(s, 3H), 2.29(s, 3H), 2.39 (s, 3H), 3.31(s, 6H), 3.68(t, 4H), 6.83(s, 2H). | |

EXAMPLE 8

REPRESENTATIVE COMPOUNDS HAVING CRF RECEPTOR BINDING ACTIVITY

Compounds were evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay was performed in 1.5 ml Eppendorf tubes using approximately $1 \times 10^6$ cells per tube stably transfected with human CRF receptors. Each tube received about 0.1 ml of assay buffer (e.g., Dulbecco's phosphate buffered saline, 10 mM magnesium chloride, 20 μM bacitracin) with or without unlabeled sauvagine, urotensin I or CRF (final concentration, 1 mM) to determine nonspecific binding, 0.1 ml of [$^{125}$I] tyrosine—ovine CRF (final concentration ~200 pM or approximately the $K_D$ as determined by Scatchard analysis) and 0.1 ml of a membrane suspension of cells containing the CRF receptor. The mixture was incubated for 2 hours at 22° C. followed by the separation of the bound and free radioligand by centrifugation. Following two washes of the pellets, the tubes were cut just above the pellet and monitored in a gamma counter for radioactivity at approximately 80% efficiency. All radioligand binding data was analyzed using a non-linear least-square curve-fitting program. Binding activity corresponds to the concentration (nM) of the compound necessary to displace 50% of the radiolabeled ligand from the receptor. The following compounds have a $K_i \leq 250$ nM: 2, 5, 8, 13, 14, 20, 28, 73, 82, 85, 86 and 87 as defined in Tables 1–5. Compound 8 was found to have the best score in this test.

EXAMPLE 9

CRF STIMULATED ADENYLATE CYCLASE ACTIVITY

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 hour at 37° C. with various concentrations of CRF-related and unrelated peptides in order to establish the pharmacological rank-order profile of the particular receptor subtype. Following the incubation, the medium is aspirated, the wells rinsed once gently with fresh medium, and the medium aspirated. To determine the amount of intracellular cAMP, 300 μl of a solution of 95% ethanol and 20 mM aqueous hydrochloric acid is added to each well and the resulting suspensions are incubated at −20° C. for 16 to 18 hours. The solution is removed into 1.5 ml Eppendorf tubes and the wells washed with an additional 200 μl of ethanol/aqueous hydrochloric acid and pooled with the first fraction. The samples are lyophilized and then resuspended with 500 μl sodium acetate buffer. The measurement of cAMP in the samples is performed using a single antibody kit. For the functional assessment of the compounds, a single concentration of CRF or related peptides causing 80% stimulation of cAMP production is incubated along with various concentrations of competing compounds ($10^{-12}$ to $10^{-6}$ M).

What is claimed is:

1. A compound represented by formula (I):

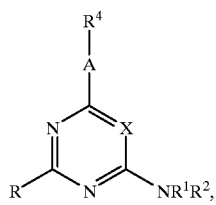

including the stereoisomers and the pharmaceutically acceptable acid addition salt forms thereof, wherein
R is $C_{1-6}$alkyl, amino, mono- or di$C_{1-6}$alkylamino;
$R^1$ is hydrogen, $C_{1-6}$alkyl, $C_{3-6}$alkenyl, hydroxy$C_{1-6}$alkyl or $C_{1-6}$alkyloxy-$C_{1-6}$alkyl;
$R^2$ is $C_{1-6}$alkyl, mono- or di$C_{3-6}$cycloalkylmethyl, phenylmethyl, substituted phenylmethyl, $C_{1-6}$alkyloxy$C_{1-6}$alkyl, hydroxy$C_{1-6}$alkyl, $C_{1-6}$alkyloxycarbonyl$C_{1-6}$alkyl, or $C_{3-6}$alkenyl;
or $R^1$ and $R^2$ taken together with the nitrogen to which they are attached may form a pyrrolidinyl, morpholinyl or piperidinyl group;
X is $CR^3$;
$R^3$ is hydrogen or $C_{1-6}$alkyl;
$R^4$ is phenyl or substituted phenyl;
A is

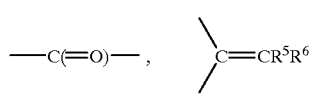

or —$CR^7R^8$—
wherein
$R^5$ and $R^6$ each independently are hydrogen or $C_{1-4}$alkyl;
$R^7$ is hydrogen or OH, $R^8$ is hydrogen or $C_{1-6}$alkyl; and
substituted phenyl is phenyl substituted with 1, 2 or 3 substituents independently selected from halo, hydroxy, $C_{1-6}$alkyloxy, benzyloxy, $C_{1-6}$alkylthio, trifluoromethyl, $C_{1-6}$alkyl and cyano.

2. The compound of claim 1 wherein $R^1$ is hydrogen, $C_{1-6}$alkyl or $C_{3-6}$alkenyl; $R^2$ is $C_{1-6}$alkyl, $C_{3-6}$cycloalkylmethyl, hydroxy$C_{1-6}$alkyl, $C_{3-6}$alkenyl, or $C_{1-6}$alkyloxycarbonyl$C_{1-6}$alkyl;
or $R^1$ and $R^2$ taken together with the nitrogen atom to which they are attached may form a pyrrolidinyl, morpholinyl or piperidinyl group.

3. The compound according to claim 2 wherein R is amino or $C_{1-4}$alkyl, $R^3$ is hydrogen or $C_{1-4}$alkyl, $R^4$ is phenyl substituted with 2 or 3 substituents selected from halo, $C_{1-4}$alkyloxy and $C_{1-4}$alkyl.

4. The compound according to claim 3 wherein R is $C_{1-2}$alkyl; $R^1$ is $C_{2-4}$alkyl or $C_{3-4}$alkenyl; $R^2$ is $C_{2-4}$alkyl, $C_{3-4}$alkenyl, cyclopropylmethyl, or hydroxy$C_{2-4}$alkyl; $R^3$ is $C_{1-2}$alkyl; $R^4$ is phenyl substituted with 2 or 3 substituents selected from methoxy and $C_{1-2}$alkyl.

5. The compound according to claim 1 wherein X is $CR^3$, wherein $R^3$ is $C_{1-2}$alkyl, R is $C_{1-2}$alkyl, $R^1$ is $C_{2-4}$alkyl, $R^2$ is cyclopropylmethyl, $R^4$ is phenyl di-or trisubstituted in the 2,4,6-position with $C_{1-2}$alkyl or methoxy and A is —CO— or —$CH_2$—.

6. The compound according to claim 5 wherein $R^3$ and R are methyl and $R^1$ is n-propyl.

7. A pharmaceutical composition comprising a compound as claimed in claim 1 in combination with a pharmaceutically acceptable carrier or diluent.

8. A method of antagonizing a CRF receptor in a warm-blooded animal, comprising administering to the animal an effective amount of a compound as claimed in claim 1.

9. A method of treating a disorder manifesting hypersecretion of CRF in a warm-blooded animal, comprising administering to the animal an effective amount of a compound as claimed in claim 1.

10. The method of claim 9 wherein the disorder is selected from depression, an anxiety-related disorder, a feeding disorder, stress-induced immune suppression, stroke, Cushing's disease, infantile spasms, epilepsy, seizure, and an inflammatory condition.

11. The method of claim 10 wherein the disorder is anorexia nervosa, bulimia or irritable bowel syndrome.

12. A process of preparing a composition as claimed in claim 7 wherein the active ingredient is intimately mixed with the carrier or diluent.

13. A process of preparing a compound as claimed in claim 1 characterized in that
a) a pyrimidine or triazine of formula (II) is reacted with an amine $HNR^1R^2$:

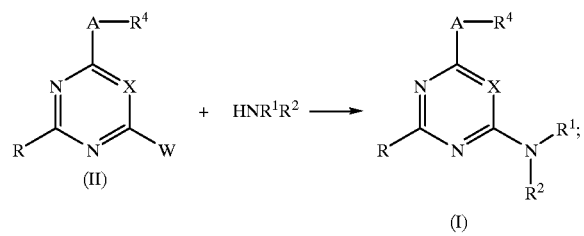

b) a pyrimidine or triazine of formula (III) is reacted in a Grignard reaction with $R^4$—Mg-halo, wherein halo represents a halogen atom, thus preparing compounds of formula (I-a) which may be converted to compounds of formulae (I-b) or (I-c) by reacting (I-a) with a Grignard reagent $R^5R^6CH$—Mg-halo yielding compounds of formula (I-b), which in turn is converted to a compound of formula (I-c) by a dehydration reaction; or a compound of formula (I-a) is converted to a compound of formula (I-d) by a reduction reaction;

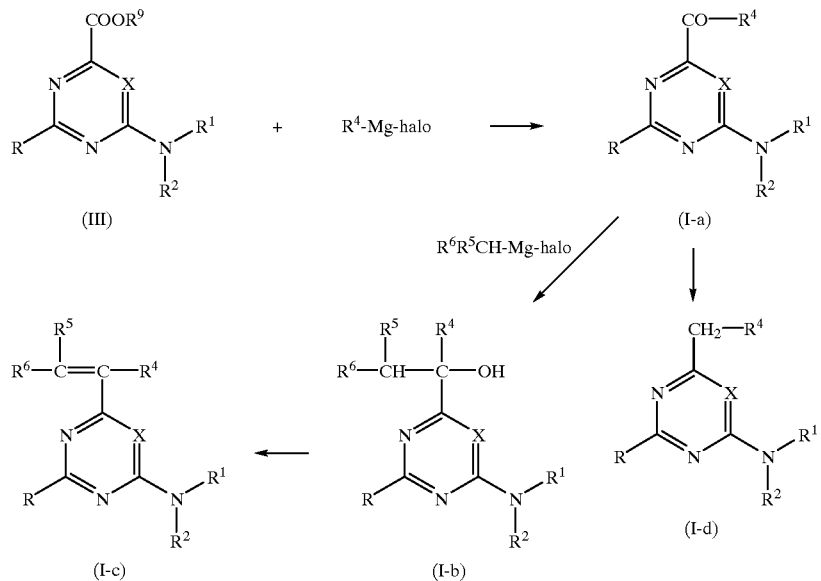

c) a thiourea of formula (IV) is reacted with a a compound of formula (V), thus preparing a compound of formula (I-e):

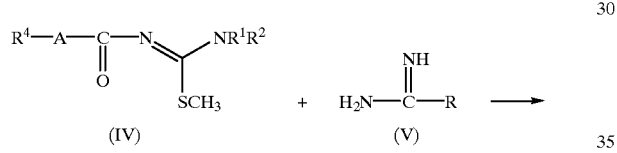

d) an intermediate (VI) is reacted with a Grignard reagent $R^4$—Mg-halo, thus yielding a compound (I-f):

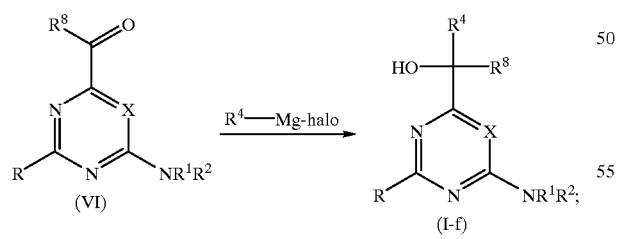

e) a compound (I-a) is reacted with a Grignard reagent $R^8$—Mg-halo thus yielding a compound (I-f);

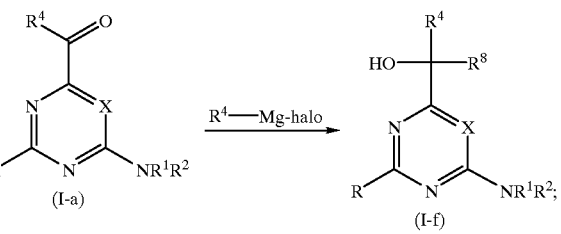

f) a compound (I-f) is reduced to a compound (I-g):

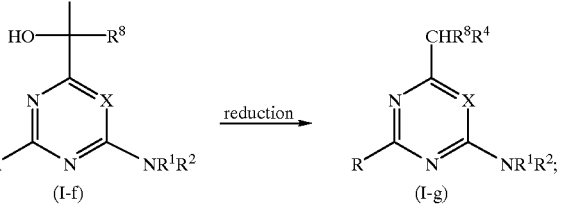

wherein in the above reaction schemes the various radicals have the meanings as defined in claim 1 and W is a leaving group;

and converting the compounds of formula (I) into each other following art-know functional group transformation reactions; and if desired, preparing acid-addition salt forms by treating the compounds of formula (I) with an appropriate acid.

* * * * *